United States Patent
Saxena et al.

(10) Patent No.: US 8,518,399 B2
(45) Date of Patent: Aug. 27, 2013

(54) METHODS OF TREATING INFECTIONS ORIGINATING FROM VIRUSES IN THE HERPESVIRIDAE FAMILY

(75) Inventors: Shailendra K. Saxena, Monroe Township, NJ (US); Wojciech Ardelt, New City, NY (US)

(73) Assignee: Tamir Biotechnology, Inc., San Diego, CA (US)

( * ) Notice: Subject to any disclaimer, the term of this patent is extended or adjusted under 35 U.S.C. 154(b) by 85 days.

(21) Appl. No.: 12/948,026

(22) Filed: Nov. 17, 2010

(65) Prior Publication Data

US 2012/0121569 A1    May 17, 2012

(51) Int. Cl.
*A61K 38/46* (2006.01)

(52) U.S. Cl.
USPC .......................................................... 424/94.6

(58) Field of Classification Search
None
See application file for complete search history.

(56) References Cited

U.S. PATENT DOCUMENTS

2009/0246214 A1 * 10/2009 Goldenberg et al. ...... 424/184.1

OTHER PUBLICATIONS

Suhasini et al., Transfer RNA cleavages by onconase reveal unusual cleavage sites, 2006, J Biol Chem. 281(18): 12201-9.*

* cited by examiner

*Primary Examiner* — Jon P Weber
*Assistant Examiner* — Robert Yamasaki
(74) *Attorney, Agent, or Firm* — Mark H. Jay

(57) ABSTRACT

Three RNases (ranpirnase, the second embodiment disclosed in U.S. Pat. No. 5,728,805, and recombinant Amphinase-2) are tested against identified herpesviridae infections. With some exceptions, quantitative PCR assays indicate that the RNases have anti-viral activity against many of these viruses.

6 Claims, 3 Drawing Sheets

Figure 1
Activity of Ranpirnase Against Identified Herpesviridae Infections

| Virus Tested | Test Compound | | | Control Drug | | |
|---|---|---|---|---|---|---|
| Name | EC₅₀ µM | CC₅₀ µM | SI | EC₅₀ µM | CC₅₀ µM | SI |
| Herpes simplex virus-1 | 0.31 | >10 | >32 | 0.62 | >444 | >716 |
| Herpes simplex virus-2 | 2.9 | >10 | >3.4 | 0.36 | >444 | >1233 |
| Human cytomegalovirus | 0.045 | >10 | >222 | 6.27 | >392 | >62.5 |
| Epstein-Barr virus | >0.08 | 0.26 | <3.3 | 16.85 | >88.7 | >5.26 |
| Kaposi's sarcoma | 0.0016 | 0.0074 | 4.6 | 0.86 | >35.8 | >41.6 |
| Roseolovirus-6A | >0.003 | 0.0013 | 0.43 | 11.46 | >35.8 | >3.13 |
| Roseolovirus-6B | 0.007 | 0.079 | 11.3 | 4.80 | >35.8 | >7.46 |

Control drugs were:
acyclovir ("ACV") for Herpes simplex virus-1, Herpes simplex virus-2 and Epstein-Barr virus ganciclovir ("GCV") for Human cytomegalovirus, and
cidofovir ("CDV") for Kaposi's sarcoma and Roseolovirus-6A and Roseolovirus-6B

Figure 2

Activity of Ranpirnase Variant ("'805 variant", Val$_{17}$, Asn$_{28}$, Arg$_{100}$ – Ranpirnase) Against Identified Herpesviridae Infections

| Virus Tested | Test Compound | | | Control Drug | | |
|---|---|---|---|---|---|---|
| Name | EC$_{50}$ µM | CC$_{50}$ µM | SI | EC$_{50}$ µM | CC$_{50}$ µM | SI |
| Herpes simplex virus-1 | 0.62 | >8.5 | >13.7 | 0.62 | >444 | >716 |
| Herpes simplex virus-2 | 1.2 | >8.5 | >7.1 | 0.36 | >444 | >1233 |
| Human cytomegalovirus | 0.04 | >8.5 | >213 | 6.27 | >392 | >62.5 |
| Epstein-Barr virus | >0.08 | 0.22 | <2.8 | 16.85 | >88.7 | >5.26 |
| Kaposi's sarcoma | 0.00068 | 0.006 | 8.8 | 0.86 | >35.8 | >41.6 |
| Roseolovirus-6A | 0.003 | 0.001 | 0.33 | 11.46 | >35.8 | >3.13 |
| Roseolovirus-6B | 0.0075 | 0.11 | 14.7 | 4.80 | >35.8 | >7.46 |

Control drugs were:
acyclovir ("ACV") for Herpes simplex virus-1, Herpes simplex virus-2 and Epstein-Barr virus ganciclovir ("GCV") for Human cytomegalovirus, and
cidofovir ("CDV") for Kaposi's sarcoma and Roseolovirus-6A and Roseolovirus-6B

Figure 3

Activity of recombinant Amphinase 2 ("rAmphinase 2") Against Identified Herpesviridae Infections

| Virus Tested | Test Compound | | | Control Drug | |
|---|---|---|---|---|---|
| Name | $EC_{50}\,\mu M$ | $CC_{50}\,\mu M$ | SI | $EC_{50}\,\mu M$ | $CC_{50}\,\mu M$ | SI |
| Herpes simplex virus-1 | >10 | >10 | 0 | 0.62 | >444 | >716 |
| Herpes simplex virus-2 | >10 | >10 | 0 | 0.36 | >444 | >1233 |
| Human cytomegalovirus | 0.27 | >10 | >37 | 6.27 | >392 | >62.5 |
| Epstein-Barr virus | >0.08 | 0.36 | <4.5 | 16.83 | >88.7 | >5.26 |
| Kaposi's sarcoma | 0.0036 | 0.0085 | 2.4 | 0.86 | >35.8 | >41.6 |
| Roseolovirus-6A | 0.0034 | 0.0045 | 1.3 | 11.46 | >35.8 | >3.13 |
| Roseolovirus-6B | 0.037 | 0.84 | 22.7 | 4.80 | >35.8 | >7.46 |

Control drugs were:
acyclovir ("ACV") for Herpes simplex virus-1, Herpes simplex virus-2 and Epstein-Barr virus
ganciclovir ("GCV") for Human cytomegalovirus, and
cidofovir ("CDV") for Kaposi's sarcoma and Roseolovirus-6A and Roseolovirus-6B

METHODS OF TREATING INFECTIONS ORIGINATING FROM VIRUSES IN THE HERPESVIRIDAE FAMILY

BACKGROUND OF THE INVENTION

The invention relates to infections from viruses in the herpesviridae family, and more particularly relates to treatment of such infections in living subjects. In its most immediate sense, the invention relates to treatment of such infections using certain ribonucleases (RNases), namely ranpirnase (known also by its registered trademark ONCONASE), the '805 variant of ranpirnase described below, and a recombinant variant of Amphinase 2, also described below.

Ranpirnase is an RNase. It is disclosed and claimed in U.S. Pat. No. 5,559,212. It has been tested and found to be cytotoxic to cancer cells because of its enzymatic activity against RNA. The second embodiment disclosed and claimed in U.S. Pat. No. 5,728,805 (hereinafter, the "'805 variant") is also an RNase, and has likewise been found to be cytotoxic to certain cancer cells. The '805 variant is a close variant of ranpirnase; its amino acid sequence is identical to that of ranpirnase except that it has valine instead of isoleucine at position 11, asparagine instead of aspartic acid at position 20, and arginine instead of serine at position 103. (In the drawings, the '805 variant is referred to as "$Val_{11}$, $Asn_{20}$, $Arg_{103}$-Ranpirnase".) Amphinase 2 is also an RNase. It is the protein identified as 2325p4 in U.S. Pat. No. 6,239,257 B1 and it too has been found to be cytotoxic to cancer cells. Recombinant Amphinase 2 ("rAmphinase 2") is similar to Amphinase 2, but has a Met residue at position −1 and lacks glycan moieties that are located in Amphinase 2 at positions 27 and 91. rAmphinase 2 is described in Example 1 of U.S. Pat. No. 7,229,824 B2 and has SEQ ID NO:59.

Human herpesviridae infections include inter alia herpes simplex virus-1 ("HSV-1"), herpes simplex virus-2 ("HSV-2"), human cytomegalovirus ("HCMV"), Epstein-Barr virus ("EBV"), Karposi's sarcoma ("HHV-8"), roseolovirus-6A ("HHV-6A"), and roseolovirus-6B ("HHV-6B"). These infections are conventionally treated using acyclovir ("ACV") and ganciclovir ("GCV"), but existing treatments are not satisfactory. Ganciclovir, which is approved for use in e.g. human cytomegalovirus, is toxic and poorly tolerated. Acyclovir is less toxic and less poorly tolerated, but both drugs are insufficiently active. This is of particular concern in the case of human cytomegalovirus, which frequently manifests itself in immune-compromised patients, such as those who have undergone organ or bone marrow transplants. It would be advantageous to provide a method for treating herpesviridae infections that would be less toxic, better tolerated, and more active.

Ranpirnase, the referenced '805 variant, and a rAmphinase 2 have been discovered to be surprisingly active against certain human herpesviridae infections. Ranpirnase is known to be non-toxic and well-tolerated in humans, and the two other RNases are believed to share these qualities. In accordance with the invention, various herpesviridae infections are treated using these RNases by administering them in therapeutically effective amounts.

BRIEF DESCRIPTION OF THE DRAWINGS

In the drawings, wherein $EC_{50}$ is the concentration (expressed in μM) of the test RNase that inhibited virus replication by 50%, $CC_{50}$ is the concentration (expressed in μM) of the test RNase that decreased cell viability by 50%, SI, the selective index, is $CC_{50}/EC_{50}$. The higher the value of SI, the more active is the tested RNase, Control $EC_{50}$ is the concentration (expressed in μM) of a control drug that inhibited virus replication by 50%. The control drug is either acyclovir ("ACV"), cidofovir ("CDV"), or Ganciclovir ("GCV"):

FIG. 1 shows the results of testing the anti-viral activity of ranpirnase against identified viruses belonging to the herpesviridae family;

FIG. 2 shows the results of testing the anti-viral activity of the '805 variant against identified viruses belonging to the herpesviridae family; and FIG. 3 shows the results of testing the anti-viral activity of rAmphinase-2 against identified viruses belonging to the herpesviridae family.

DETAILED DESCRIPTION OF PREFERRED EMBODIMENTS

To evaluate the activity of the three tested RNases against human herpesviridae infections, the following quantitative PCR assay was used:

Solutions of the tested RNases were prepared in cell culture medium without use of dimethyl sulfoxide ("DMSO"). DMSO is unnecessary because the tested RNases are water-soluble.

I. Evaluation Against Herpes Simplex Virus-1, Herpes Simplex Virus-2, and Human Cytomegalovirus Antiviral activity against herpes simplex virus-1, herpes simplex virus-2, and human cytomegalovirus was evaluated by cytopathic effect inhibition ("CPE-inhibition") assays in primary human foreskin fibroblast (HFF) cells. Primary HFF cells were counted and $2.5 \times 10^4$ cells per well were seeded into 96-well plates in 100 it of minimal essential medium supplemented with 10% fetal bovine serum ("FBS"). The cells were then incubated for 24 hours at 37° C. in a 5% $CO_2$ humidified incubator. Solutions of the tested RNases were added to triplicate wells to yield a final concentration of 10 μM, and diluted to yield concentrations of 2, 0.4, 0.08, 0.016, and 0.0032 μM. The plates were then incubated for 1 h and 100 μl of a virus suspension was added. Typically, 1000 plaque forming units per cell were added to each well, but this varied depending on the virus. The plates were then incubated for 3 days. Total DNA from the cultures was harvested and viral genome copy number was determined by real time PCR assays.

II. Evaluation Against Roseolovirus-6A and Roseolovirus-6B

Antiviral activity against roseolovirus-6B was evaluated in Molt-3 cells. The tested RNases were diluted using methods used for the CPE-inhibition assay in RPMI 1640 medium (Roswell Park Memorial Institute) supplemented with 10% FBS, L-glutamine, penicillin and gentamicin. $2 \times 10^4$ Molt-3 cells were added to each well, and infected cells were added to achieve the desired multiplicity of infection and incubated at 37° C. for 4 days. The accumulation of viral DNA was determined by real time PCR assays. Antiviral activity against roseolovirus-6A was evaluated by similar procedures, but using HSB-2 cells.

III. Evaluation Against Karposi's Sarcoma and Epstein-Barr Virus

Efficacy against Karposi's sarcoma was assessed in 96-well plates by a standard laboratory protocol similar to the validated assay used with the Epstein-Barr virus. BCBL1 cells were maintained in growth medium consisting of RPMI 1640 medium supplemented with 10% FBS, penicillin, gentamicin, and L-glutamine. The compounds under test were diluted in triplicate wells of a separate 96-well plate to yield final concentrations identical to those used in the studies for herpes simplex virus-1. The Karposi's sarcoma cells were then induced to undergo a lytic infection by the addition of phorbol 12-myristate 13-acetate at a final concentration of 100 ng/ml. The plates were then incubated for 4 days and the accumulation of viral DNA was assessed by real time PCR assays. The same methods and compound concentrations were used to evaluate antiviral efficacy against Epstein-Barr virus, except that the studies were performed using Akata cells, which were induced to undergo a lytic infection by adding a F(ab')2 fragment of goat anti-human IgG antibody. The Akata cells were incubated for 4 days and the accumulation of viral DNA was determined by real time PCR assays.

For all the assays, cytotoxicity was evaluated in the same cell line used to evaluate antiviral activity and was assessed by CellTiter-Glo assays.

EVALUATION RESULTS

SI measures of the ability of the tested RNase to inhibit replication of a viral infection without killing the infected cells. Where SI in the accompanying Figures is greater than 1, the RNase under test is active against the virus indicated, and increasing values of SI indicate increasing activity. Thus, as can be seen in FIGS. 1 and 2, ranpirnase and the '805 variant are each extraordinarily active against human cytomegalovirus, while being entirely inactive against roseolovirus-6A. Other activities against other herpesviridae infections are also shown in the Figures.

Because SI measures the ability of a substance under test to inhibit replication of a particular virus without killing the infected cells themselves, it is reasonably correlated with usefulness of the substance in treating a living subject that is infected with the virus. Accordingly, test results in which SI>1 indicate that living subjects infected with the identified viruses can be treated by administration of an appropriate dose of the corresponding RNase.

Although at least one preferred embodiment of the invention has been described above, this description is not limiting and is only exemplary. The scope of the invention is defined only by the claims, which follow:

The invention claimed is:

1. A method of treating a herpesviridae infection that is other than roseolovirus-6A, comprising the step of administering to a living subject in need of such treatment a therapeutically effective amount of a polypeptide consisting of the amino acid sequence disclosed in FIG. 2 of U.S. Pat. No. 5,559,212.

2. A method of treating a herpesviridae infection that is other than roseolovirus-6A, comprising the step of administering to a living subject in need of such treatment a therapeutically effective amount of a polypeptide consisting of the amino acid sequence of SEQ ID NO:2 of U.S. Pat. No. 5,728,805.

3. A method of treating human cytomegalovirus, comprising the step of administering to a living subject in need of such treatment a therapeutically effective amount of:
   a. a polypeptide consisting of the amino acid sequence disclosed in FIG. 2 of U.S. Pat. No. 5,559,212, or
   b. a polypeptide consisting of the amino acid sequence of SEQ ID NO:2 of U.S. Pat. No. 5,728,805.

4. A method of treating roseolovirus-6B, comprising the step of administering to a living subject in need of such treatment a therapeutically effective amount of:
   a. a polypeptide consisting of the amino acid sequence disclosed in FIG. 2 of U.S. Pat. No. 5,559,212, or
   b. a polypeptide consisting of the amino acid sequence of SEQ ID NO:2 of U.S. Pat. No. 5,728,805.

5. A method of treating Epstein-Barr virus, comprising the step of administering to a living subject in need of such treatment a therapeutically effective amount of:
   a. a polypeptide consisting of the amino acid sequence disclosed in FIG. 2 of U.S. Pat. No. 5,559,212, or
   b. a polypeptide consisting of the amino acid sequence of SEQ ID NO:2 of U.S. Pat. No. 5,728,805.

6. A method of treating herpes simplex virus, comprising the step of administering to a living subject in need of such treatment a therapeutically effective amount of:
   a. a polypeptide consisting of the amino acid sequence disclosed in FIG. 2 of U.S. Pat. No. 5,559,212, or
   b. a polypeptide consisting of the amino acid sequence of SEQ ID NO:2 of U.S. Pat. No. 5,728,805.

* * * * *